United States Patent [19]
Muroki

[11] Patent Number: 5,848,985
[45] Date of Patent: Dec. 15, 1998

[54] SKIN-CONTACT TYPE MEDICAL TREATMENT APPARATUS

[75] Inventor: Masahisa Muroki, Kanazawa, Japan

[73] Assignee: Polytronics, Ltd., Ishikawa-ken, Japan

[21] Appl. No.: 797,482

[22] Filed: Feb. 6, 1997

[30] Foreign Application Priority Data

Feb. 9, 1996 [JP] Japan ................................. 8-024245

[51] Int. Cl.⁶ .................................................. A61N 1/30
[52] U.S. Cl. ............................... 604/20; 607/72; 607/76; 607/152; 429/3
[58] Field of Search ............................ 607/1, 72, 75–76, 607/115, 152; 604/20–21; 429/3

[56] References Cited

U.S. PATENT DOCUMENTS

| | | |
|---|---|---|
| 4,619,252 | 10/1986 | Ibbott . |
| 4,767,401 | 8/1988 | Seiderman . |
| 4,976,705 | 12/1990 | Aki et al. . |
| 4,976,706 | 12/1990 | Aki et al. . |
| 5,637,084 | 6/1997 | Kontturi et al. . |
| 5,685,837 | 11/1997 | Horstmann . |
| 5,772,688 | 6/1998 | Muroki . |

*Primary Examiner*—Mark Bockelman
*Attorney, Agent, or Firm*—Frishauf, Holtz, Goodman, Langer & Chick

[57] ABSTRACT

A skin-contact type medical treatment apparatus has a first conductive member having a contact surface made of single metal or alloy and a second conductive member having a contact surface made of semiconductor. The standard single-electrode potential of the semiconductor constituting the contact surface of the second conductive member is lower than a standard single-electrode potential of the metal constituting the contact surface of the first conductive member. The apparatus further includes a parallel circuit of a diode and a capacitor electrically connected to the first and second conductive members. The apparatus is used by making both the contact surfaces of the first and second conductive members in contact with skin.

12 Claims, 7 Drawing Sheets

$$I_0 = \frac{E}{R_S}$$

$$I' = \frac{E - |V_B|}{R_S}$$

SKIN-CONTACT TYPE MEDICAL TREATMENT APPARATUS

BACK OF THE INVENTION

1. Field of the Invention

The present invention relates to a skin-contact type medical treatment apparatus capable of relieving unidentified complaint syndrome through subcutaneous current flow and transcutaneously dosing medicine.

2. Description of the Related Art

As the stresses of modern life and the number of elderly persons increase, patients having unidentified complaint syndrome such as shoulder stiffness and waist pains are increasing. Some information indicates the number of patients has reached a half of the national population. Patients having various types of chronic diseases are also increasing.

For medical treatment of such unidentified complaint syndrome and chronic diseases, physical stimuli transcutaneously applied to the diseased part or transcutaneous dosing are known as effective.

For medical treatment of unidentified complaint syndrome, transcutaneous stimuli are applied to the tissues (muscle and peripheral nervous system) of a diseased part, mainly aiming at activating metabolism. For this purpose, physical curing prevails among patients, typically massage, acupuncture and moxibustion, subcutaneous current flow, and heating. For medical treatment of inflammation such as pains and boils, transcutaneous dosing of antiphlogistic or anodyne is widely used.

Transcutaneous dosing has advantages that local or constant density dosing is possible. Its use is widespread among some chronic patients necessary to dose heart attack drug, antibiotic drug, hormone drug, epileptic drug, or the like. The present inventor has developed an ion permeating apparatus which forms a bio-cell when it is made in contact with skin and can relieve fatigues of muscles and nerves through subcutaneous current flow generated by a weak d.c. power (Japanese Patents Nos. 1388949, 1427360, 1631137, Japanese Utility Model No. 1922166, and others). This bio-cell is a chemical cell formed by a combination of a metal electrode with large electron affinity for forming the positive pole of the cell and a negative metal electrode with small electron affinity for forming the negative pole of the cell. By incorporating this principle, the inventor has developed a transcutaneous dosing element (JP-A 3-16573 and others).

In use of this transcutaneous dosing element, conductive matrix containing negative ions to be dosed, the matrix being disposed under a metal electrode for forming the positive pole of a cell, and a semiconductor electrode disposed near the matrix for forming the negative pole of the cell, are both made in contact with skin, both the metal electrode and semiconductor electrode being electrically connected externally. Therefore, a closed circuit is formed which is partially constituted of the conductive matrix containing medicine ions to be dosed. The chemical cell starts flowing current so that iontophoresis occurs between the conductive matrix and the skin to accelerate subcutaneous permeation of medicine. The electrodes, medicine layer, and plaster are formed into a laminated sheet. Therefore, an electric field acceleration type transcutaneous dosing element which is safe, stable, and inexpensive can be realized. This sheet type medical treatment apparatus is convenient for portable use. The inventor has also developed technologies which can enhance synaptic plasticity of a peripheral nervous system, and can induce the long term potentiation (LTP effects) to improve a physiological activation degree. With these technologies, small voltage pulse waves in a frequency band of 50 to 500 Hz are applied transcutaneously to peripheral nerves, by superposing the pulse voltage upon the d.c. power of the bio-cell or by intermittently flowing subcutaneous current from the bio-cell. By incorporating these technologies, the curing effects of unidentified complaint syndrome can be improved, and the transcutaneous absorption rate of medicine can be improved considerably through iontophoresis.

If a series of small voltage pulse waves (tetanic stimulation or tetanus) in the frequency band of 50 to 500 Hz is applied in addition to flowing subcutaneous current from the bio-cell, physiological activation of skin tissues can be achieved. Conventionally, a pulse oscillation circuit and its power source are necessary for applying tetanus. If a compact pulse oscillation circuit is fabricated by using semiconductor technologies such as integrated circuits, small voltage pulses can be generated by using a compact and light external power source such as a button battery. Therefore, a portable tetanus support type transcutaneous dosing element can be manufactured.

However, since the semiconductor integrated circuit and a button battery are high in cost, it is practically difficult to use the transcutaneous dosing element assembled with these high cost circuit and battery as a disposable element.

A plurality of ion permeating apparatuses for medical treatment of unidentified complaint syndrome are commonly used by attaching them to skin. Use of pulse oscillation circuits connected to these ion permeating apparatuses is not desirable from the viewpoint of practical use although they are compact and light. Furthermore, since a compact dry battery such as a button battery self-discharges, if the battery built in the pulse oscillation circuit is left unused for a long period of time, the voltage lowers and the battery may become unusable.

SUMMARY OF THE INVENTION

It is an object of the present invention to provide a disposable skin-contact type medical treatment apparatus with a built-in, compact, light, and inexpensive pulse oscillation circuit for producing tetanus which enhance the efficacy of a medical treatment apparatus for unidentified complaint syndrome or of a transcutaneous dosing element, respectively using a bio-cell.

It is another object of the present invention to provide a skin-contact type medical treatment apparatus with a pulse current flow type bio-cell capable of suppressing ill after-effects while maintaining a high curing rate, without incorporating a d.c. current flow type bio-cell having a high rate of ill after-effects through subcutaneous current flow.

According to one aspect of the present invention, there is provided a skin-contact type medical treatment apparatus comprising: a first conductive member having a contact surface made of single metal or alloy; a second conductive member having a contact surface made of semiconductor, a standard single-electrode potential of the semiconductor constituting the contact surface of the second conductive member being lower than a standard single-electrode potential of the metal constituting the contact surface of the first conductive member; and a parallel circuit of a diode and a capacitor electrically connected to the first and second conductive members.

As the contact surfaces of the first and second conductive members are both made in contact with skin, an electrically closed circuit is formed being constituted of the first conductive member, skin, second conductive member, and a parallel circuit of the capacitor and diode. Current flows in this closed circuit because of a difference of standard single-electrode potential between substances constituting the contact surfaces of the first and second conductive members. The parallel circuit of the diode and capacitor functions to make the capacitor repeat charge/discharge at a predetermined period and flow subcutaneous current of a pulse waveform. Current flow of a pulse waveform can efficiently relieve unidentified complaint syndrome or cause transcutaneous dosing of medicine ions.

DETAILED DESCRIPTION OF THE PREFERRED EMBODIMENTS

Figure 3A:
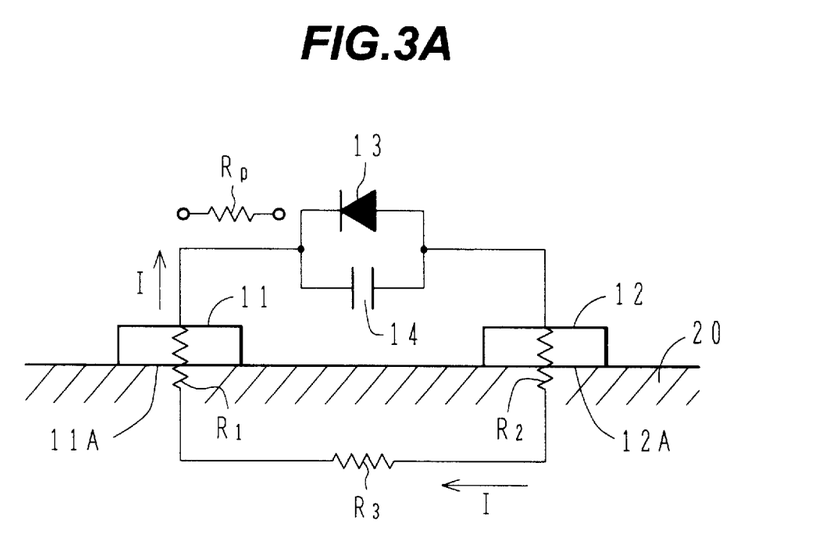
FIGS. 3A is a closed circuit diagram formed when the skin-contact type medical treatment apparatus is made in contact with skin.
Figure 3B:
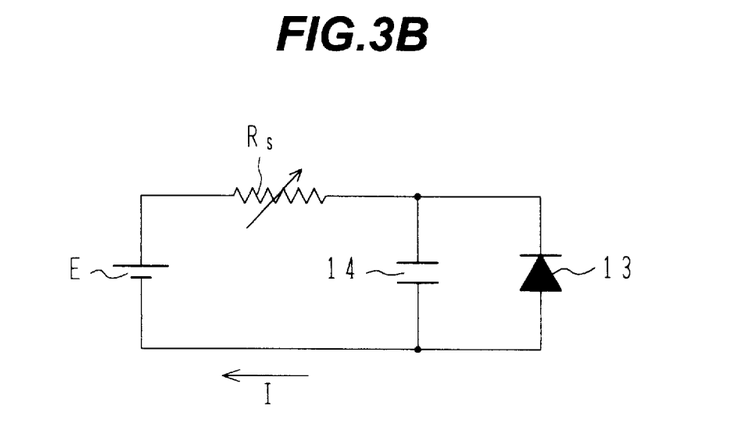
FIG. 3B is an equivalent circuit diagram of the closed circuit shown in FIG. 3A.

The principles on which embodiments of the invention are based will first be described. FIGS. 3A and 3B are circuit diagrams of a skin-contact type medical treatment apparatus according to an embodiment. Referring to FIG. 3A, a first conductive member 11 and a second conductive member 12 are electrically connected by a parallel circuit of a diode 13 and a capacitor 14. The first and second conductive members 11 and 12 have surfaces 11A and 12A which can contact skin 20. These surfaces 11A and 12A are called a contact surface. For example, the first conductive member 11 is metal and the second conductive member 12 is semiconductor. A standard single-electrode potential of the metal constituting the contact surface of the first conductive member 11 is higher than that of the semiconductor constituting the contact surface of the second conductive member 12. If the contact surfaces 11A and 12A of the first and second conductive members 11 and 12 are made in contact with the skin 20, a closed circuit shown in FIG. 3A is formed. It is necessary to consider, as a load of this closed circuit, a skin contact resistance $R_1$ of the first conductive member 11, a skin contact resistance $R_2$ of the second conductive member 12, and a subcutaneous impedance $R_3$, in addition to the diode 13 and capacitor 14. The skin contact resistances $R_1$ and $R_2$ and the subcutaneous impedance $R_3$ change depending upon individuals and skin contact areas as well as physiological activation degrees. As the physiological activation degree at a skin contact area becomes high, the resistance or impedance tends to lower by about one digit. A protective resistor with a resistance of $R_P$ may be connected serially to the parallel circuit of the diode 13 and capacitor 14 in order to suppress ill after-effects such as boils to be produced by electric stimuli if the physiological activation degree is high. The protective resistance $R_P$ is in series with the skin contact resistances $R_1$ and $R_2$ and with the subcutaneous impedance $R_3$. FIG. 3B is an equivalent circuit diagram of the bio-cell with a load shown in FIG. 3A, wherein a resistance $R_S$ is given by:

$$R_S = R_1 + R_2 + R_3 \tag{1}$$

If the protective resistance $R_P$ is used, the resistance $R_S$ is given by:

$$R_S = R_1 + R_2 + R_3 + R_P \tag{2}$$

In FIG. 3B, a d.c. power E corresponds to an internal electromotive force of a bio-cell formed when the first and second conductive members 11 and 12 are made in contact with the skin 20, respectively as the positive and negative poles of the cell. A maximum value of the internal electromotive force is basically determined by selected materials of the first and second conductive members 11 and 12. The direction of connecting the diode 13 is changed in accordance with a relationship between absolute values of a diode forward current rise voltage $V_F$ and a diode backward breakdown voltage $V_B$. The direction of the diode 13 shown in FIG. 3B is used when $|V_B| > |V_F|$.

Figure 4A:
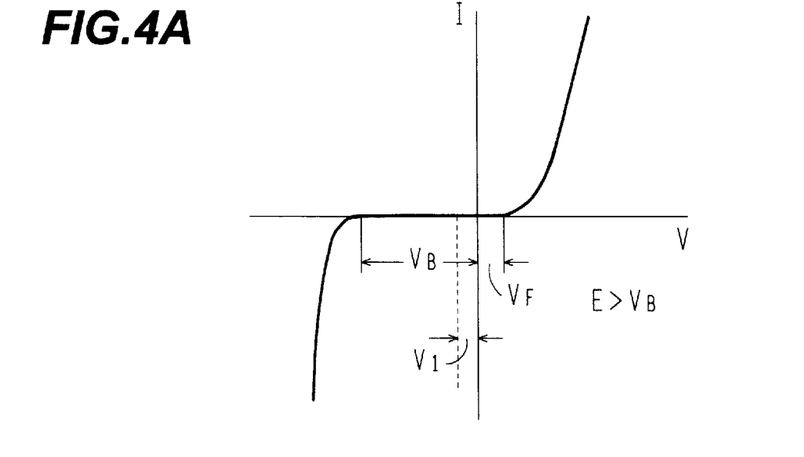
FIG. 4A is a graph showing the rectification characteristics of a diode shown in FIG. 3B.

FIG. 4A is a graph showing the rectification characteristics of the diode 13. It is necessary to select the backward breakdown voltage $V_B$ lower than the internal electromotive force E of the bio-cell. $V_B$ can be set smaller than 0.6 V by adjusting impurity concentrations of a constant voltage diode such as a Ge Zener diode.

Figure 4B:
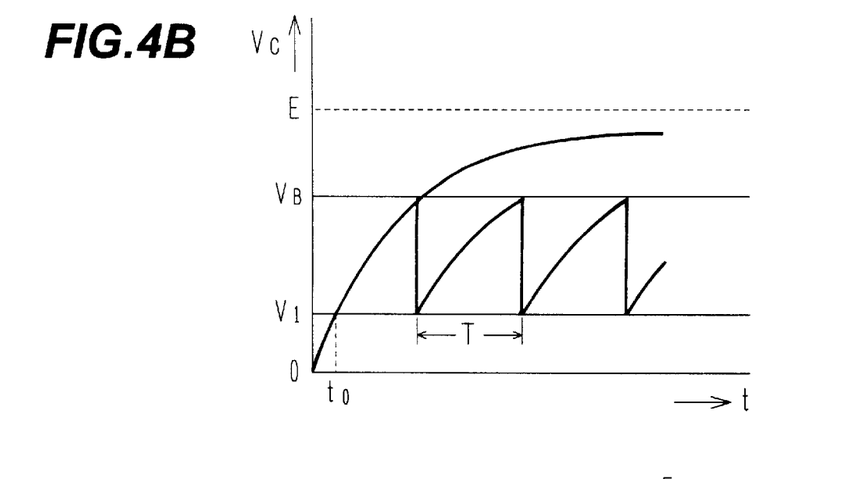
FIG. 4B is a graph showing a change in the voltage across a capacitor shown in FIG. 3B.

A change in the voltage $V_C$ across the capacitor 14 is shown in FIG. 4B. After the apparatus is made in contact with the skin, charge current flows through the capacitor 14 and the voltage $V_C$ starts rising. Breakdown of the diode 13 occurs at $V_C = V_B$. Charges accumulated in the capacitor 14 are discharged via the diode 13 and the voltage $V_C$ lowers. In this case, the diode 13 does not enter the non-conductive state at once, but reverse current flows transiently. This reverse current stops at $V_C = V_1$. Since the time constant of the closed circuit constituted of the capacitor 14 and diode 13 is short, the conduction period of the diode 13 is sufficiently shorter than the period while the capacitor 14 is charged via the resistor $R_S$. When the diode 13 becomes non-conductive, charge current flows again through the capacitor 14 and the voltage $V_C$ rises. This operation is repeated so that the voltage $V_C$ has a sawtooth pulse waveform. A voltage $V_1$ at which the breakdown is terminated may be 0 volt in some cases.

Figure 4C:
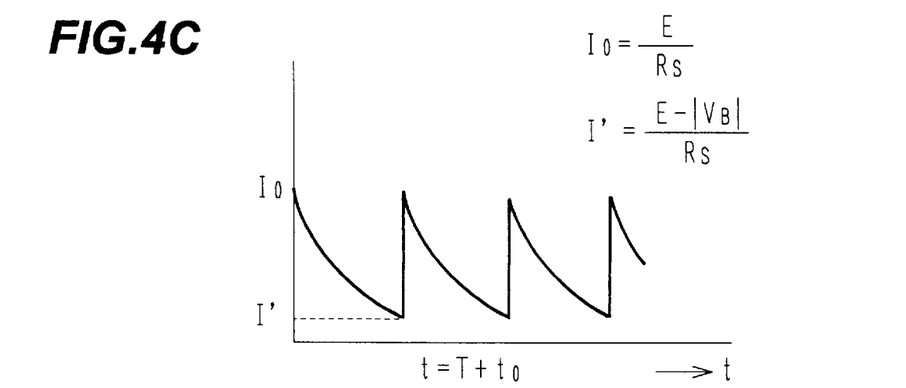
FIG. 4C is a graph showing a change in the current flowing in the closed circuit shown in FIG. 3B.

FIG. 4C shows a change in the circuit current I corresponding to the change in the voltage $V_C$ show in FIG. 4B. As seen from FIG. 4C, the circuit current I reduces exponentially as the capacitor 14 is charged, and the circuit current I takes the initial value as the capacitor 14 discharges. The pulse period T is given by:

$$T = R_S C \cdot \ln\{(E-V_1)/(E-V_B)\} \quad (3)$$

where C is the capacitance of the capacitor 14. As described earlier, the internal electromotive force E of the bio-cell is generally determined by a combination of materials of the first and second conductive members 11 and 12, and is about 1 to 3 V. The subcutaneous impedance Rs is often about 1MΩ.

If the diode 13 is a so-called backward diode with $|V_B|<|V_F|$, the direction of the diode 13 shown in FIG. 3B is reversed. Also in this case, it is necessary to satisfy the relationship of $E > V_F$ in order to maintain pulse oscillation.

In order to relieve electrical stimuli to be produced by a rise of the physiological activation degree of skin if the skin-contact type medical treatment apparatus is used for a long term at the same diseased part of the skin, it is preferable to set $V_B$ (in the case of $|V_B| \geq |V_F|$) or $V_F$ (in the case of $|V_F|<|V_B|$) to 0.5 V or lower, or more preferable 0.4 V or lower.

As shown in FIGS. 4B and 4C, current flow of a bio-cell can be pulsated at a constant period without using an external power and a complicated pulse oscillation circuit. The pulse frequency 1/T is given by the equation (3). If the capacitance of the capacitor 14 is properly set, a series of pulses of a small voltage in a frequency band of 50 to 500 Hz can be generated. A series of pulses in this frequency band applied to a subcutaneous peripheral nervous system can provide the LTP effects (long term potentiation of synaptic plasticity) by tetanic stimulation.

The skin-contact type medical treatment apparatus shown in FIG. 3A is used for medical treatment of unidentified complaint syndrome, for promotion of skin metabolism, and for medical treatment of skin disease, by making the first and second conductive members 11 and 12 in contact with skin. Even if a conductive medicine layer is disposed just under the contact surface 11A or 12A of the first and second conductive member 11 or 12 and made in contact with skin, the equivalent circuit of FIG. 3B and the voltage and current waveforms of FIGS. 4B and 4C can be used. Only the different point is an addition of impedance of the conductive medicine to the circuit resistance $R_S$ shown in FIG. 3B. Generally, the conductive medicine layer is made of matrix of ions and water soluble components for maintaining humidity. Therefore, the skin contact resistance ($R_1$ or $R_2$) of the conductive medicine layer becomes smaller than that of the first or second conductive member in direct contact with skin.

It is possible to greatly lower the skin contact resistance ($R_1$ or $R_2$) of the first or second conductive member without the conductive medicine layer, by inserting solid electrolyte tightly between skin and the first (or second) conductive member not contact with the medicine layer.

By inserting the protective resistor $R_P$ shown in FIG. 3A, ill after-effects to be produced by an increase of current flow can be suppressed. A skin contact resistance, when electrodes of a bio-cell constituted of only the first and second conductive members are made in contact with skin, is about 1 to 10MΩ which is a sum of $R_1+R_2+R_3$ shown in FIG. 3A. However, there occurs a phenomenon that $R_S=R_1+R_2+R_3$ lowers by about one digit because the skin contact resistance $R_1$ (or $R_2$) lowers considerably as the physiological activation degree is improved or a conductive medicine layer is added. If only the skin contact resistance of the electrodes of a bio-cell is taken into consideration, subcutaneous current may increase greatly. To prevent this, the protective resistor $R_P$ of 1 to 10MΩ is inserted to make an increase of subcutaneous current lower than a threshold value. In this manner, ill after-effects can be suppressed.

As the age of a patient becomes higher, the skin resistance $R_1$, $R_2$, measured when the skin-contact type medical treatment apparatus is loaded, increases more. The circuit resistance $R_S$ was 20 to 50MΩ in some cases. In such cases, it becomes necessary to set a low capacitance C in order to retain an $R_S C$ product which gives a predetermined pulse frequency. Namely, the capacitance of 5 to 20 pF of the capacitor is required to be as low as about 1 pF. Such a low capacitance can be obtained by using serially connecting capacitors sold in markets. However, this method is not always preferable because the size becomes large and cost increases. In such a case, a junction capacitance of a diode can be used effectively as the capacitor. Namely, a diode is connected in place of the capacitor. There are commercially available small and inexpensive diodes satisfying the above condition. The diode 13 in FIG. 3A can be used as the capacitor without connecting another diode.

The main object of generating pulse waves by using a combination of the diode and capacitor is to provide the LTP effects of synapses through tetanus (stimuli by highly repetitive pulses) in the pulse frequency band of 50 to 500 Hz and induce physiological skin activation from the LTP effects. From the viewpoint of this frequency band, a preferable minimum value of a $R_S C$ product is about 0.002 seconds, assuming that the bio-cell electromotive force E and the pulse peak voltage $V_B$ take minimum values of E=0.7 V and $V_B$=0.5 V in practical use. A preferable maximum value of a RsC product is about 0.1 second, assuming that E and $V_B$ take maximum values of E=2 V and $V_B$=0.8 V in practical use.

Embodiments of the invention will be detailed below.

Figure 1A:
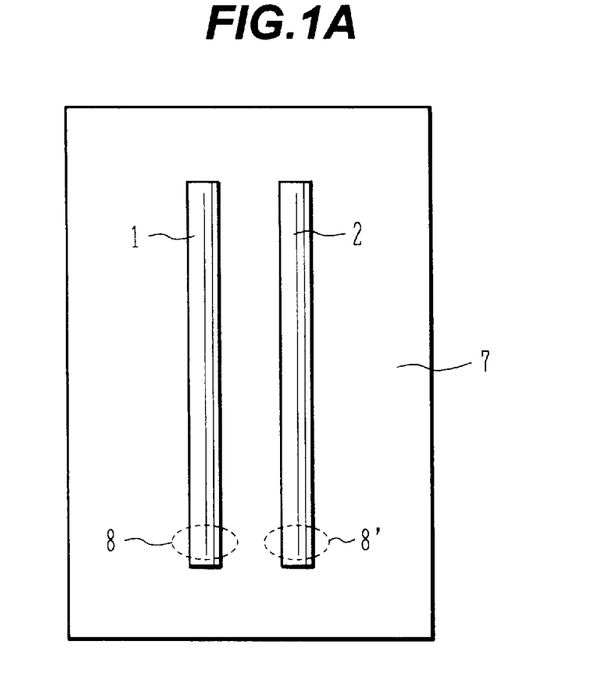
FIGS. 1A and 1B are a plan view and a side view showing the structure of a skin-contact type medical treatment apparatus according to an embodiment of the invention.
Figure 1B:
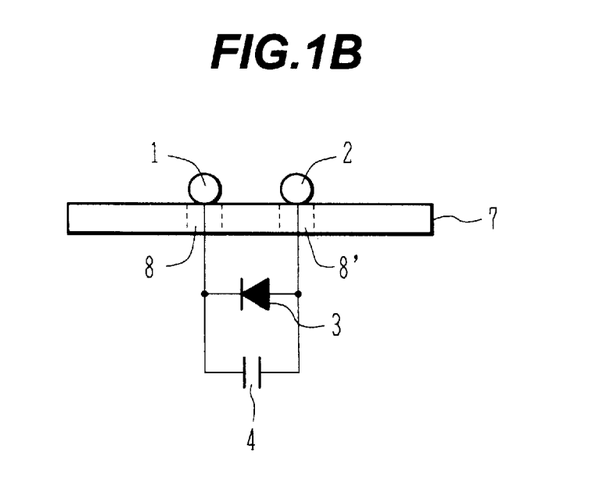

FIGS. 1A and 1B are a plan view and a side view of a skin-contact type medical treatment apparatus according to an embodiment of the invention.

First and second conductive stripe members 1 and 2 are spaced by 2 to 3 mm and adhered in parallel to an adhesive surface of a sticking cloth 7. Typically, the first conductive member 1 is a copper wire whose surface is plated with gold, and has a diameter of about 0.4 to 0.6 mm and a length of about 5 cm. The second conductive member 2 is a copper wire whose surface is covered with a zinc oxide film, and has a diameter of about 0.4 to 0.6 mm and a length of about 5 cm. Through holes 8 and 8' having a diameter of 1 mm are formed in the sticking cloth 7 near at one ends of the first and second conductive members 1 and 2. A parallel circuit of a diode 3 and a capacitor 4 mounted on the non-adhesive surface of the sticking cloth 7 electrically connects the first and second conductive members 1 and 2 via the through holes 8 and 8'. Specifically, the one end portions of the first and second conductive members 1 and 2 are inserted into the through holes 8 and 8' and bent to the non-adhesive surface of the sticking cloth 7. The bent portions are connected to the diode 3 and capacitor 4. This connection method is effective for manufacture. In this embodiment, the positive pole of the bio-cell is gold, and the negative pole is zinc oxide (n-type semiconductor). The diode is a Ge Zener diode having a backward breakdown voltage of 0.5 V, and the capacitance of the capacitor 4 is 10 pF.

The skin-contact type medical treatment apparatus shown in FIGS. 1A and 1B was fixed to a right shoulder of a patient by using the adhesive surface of the sticking cloth 7, and a change in the voltage across the capacitor was measured with a syncroscope. A change in the voltage having approximately sawtooth waveform such as shown in FIG. 4A was observed. $V_B$ was 0.5 V and $V_1$ was about 0 V. The pulse period T and pulse frequency changed with time and individuals. Several patients were used for measurements. The pulse frequency immediately after loading the apparatus was 25 to 173 Hz, whereas a rise of the pulse frequency was observed by all patients after 5 hours after loading the apparatus. This phenomenon may be ascribed to improvement of physical activation degree.

Two apparatuses shown in FIGS. 1A and 1B were loaded for 24 hours on each of twenty patients having stiffness in shoulders. The results are shown in Table 1.

TABLE 1

Cure Test of Shoulder Stiffness I

| Curing Result | Patient No. | Rate % | Pulse Freq. Hz When loading | After 24 h |
|---|---|---|---|---|
| Very effective | 14 | 70 | 126 | 345 |
| Effective | 4 | 20 | 69 | 139 |
| Not effective | 2 | 10 | 18 | 32 |

As seen from Table 1, the shoulder stiffness curing rate of the skin-contact type medical treatment apparatus reached 90%. It is to be noted that a group having a high skin contact resistance and a corresponding low pulse frequency has generally a low curing rate. In all groups, a rise of the pulse frequency was observed after 24 hours of skin contact and improvement on the physiological activation degree of skin was confirmed. However, relieving shoulder stiffness was improved less at the pulse frequency of 50 Hz or lower. All patients had no skin damages (such as boils and burns) by subcutaneous current flow.

For comparison, the diode 3 and capacitor 4 of the skin-contact type medical treatment apparatus shown in FIGS. 1A and 1B were disconnected and the first and second conductive members 1 and 2 were directly connected on the non-adhesive surface of the sticking cloth 7. Two of such apparatuses were attached to the diseased part of each of twenty patients having shoulder stiffness, for 24 hours to check the curing results. Six patients were very effective, seven patients were effective, and seven patients were not effective, and the effective curing rate lowered to 65%. Eight patients (40%) had skin damages presumably by subcutaneous current stimuli.

The above cure test data indicates that skin damages can be suppressed by controlling a cell electromotive force applied to skin by using non-linearity of the diode, during subcutaneous current stimuli by the bio-cell. Furthermore, the subcutaneous current is converted into a series of pulse waves by the combination of the diode and capacitor and the pulse frequency is set in the frequency band of 50 to 500 Hz which induces the LTP effects of synapses. Therefore, the above cure test data also indicates that the physiological activation of skin tissues can be enhanced considerably and the effects of relieving shoulder stiffness can be improved.

Figure 2A:
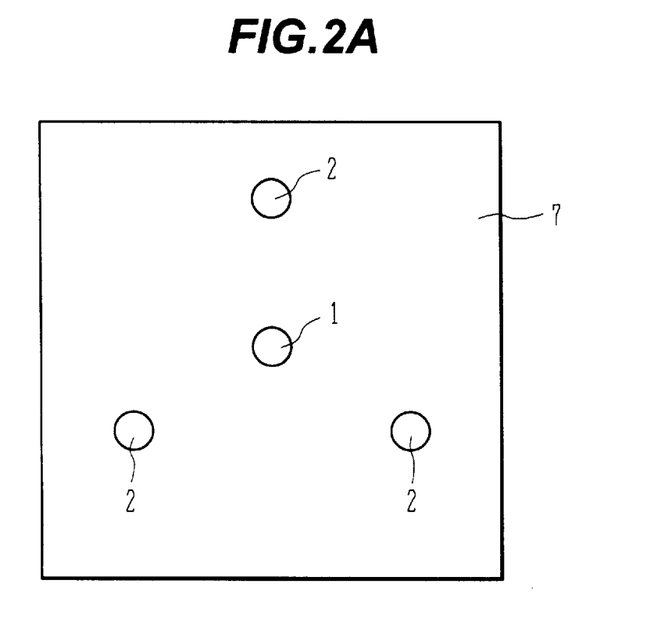
FIGS. 2A and 2B are a plan view and a side view showing the structure of a skin-contact type medical treatment apparatus according to another embodiment of the invention.
Figure 2B:
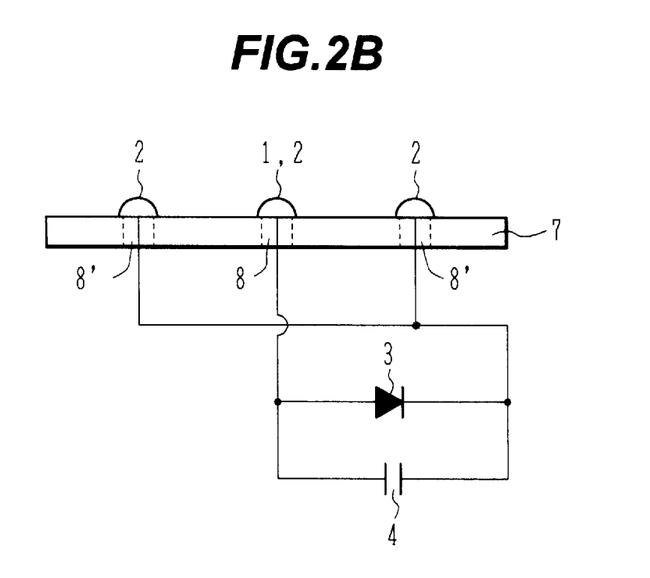

FIGS. 2A and 2B are a plan view and a side view showing the structure of a skin-contact type medical treatment apparatus according to another embodiment of the invention. In FIGS. 2A and 2B, like elements to those of the first embodiment are represented by using identical reference numerals.

In this embodiment, as shown in FIG. 2A, a second conductive member 2 of a semisphere (2.6 mm in diameter) is adhered to the adhesive surface of a sticking cloth 2 at each apex of an equilateral triangle (10 mm in side length), and a first conductive member 1 of a semisphere (2.6 mm in diameter) is adhered to the adhesive surface at the center of the equilateral triangle. The curved surface of each semisphere is oriented toward a contact surface and the flat surface thereof is adhered to the adhesive surface of the sticking cloth. Each of the second conductive members 2 is electrically connected via a parallel circuit of a diode 3 and a capacitor 4 to the first conductive member 1 on the side of the non-adhesive surface of the sticking cloth 7. As shown in FIG. 2B, electrical connection of the first and second conductive members 1 and 2 is achieved via through holes formed in the sticking cloth 7 just under the members.

The first conductive member 1 is gold (Au), and the second conductive members 2 are oxygen-deficiency type aluminu oxide ($Al_2O_{3-x}$) which is n-type semiconductor. $Al_2O_{3-x}$ is deposited about 0.5 $\mu$m thick on the curved surface of an Al semisphere base, by sputtering. Therefore, $Al_2O_{3-x}$ directly contacts skin. $Al_2O_{3-x}$ is not sputtered on the flat surface of the Al semisphere base. The diode 3 is a backward diode with $|V_F|>|V_B|$. A Ge backward diode has $V_B$ of about 0.2 V. Therefore, the connection direction of the diode 3 relative to the first and second conductive members 1 and 2 is opposite to the embodiment shown in FIGS. 1A and 1B. The capacitance of the capacitor 4 is 5 pF.

The theoretic electromotive force (internal electromotive force E) of an $Au/Al_2O_{3-x}$ bio-cell is higher than 2 V. Therefore, four types of backward diodes having different values of $V_F$ (0.5, 0.6, 0.7, and 0.9 V) were prepared for cure test of patients with shoulder stiffness. Five patients were allocated to each type of the diode 3 having a different $V_F$. One skin-contact type medical treatment apparatus shown in FIGS. 2A and 2B was attached to the diseased part of each patient for 24 hours. The obtained results are shown in Table 2.

TABLE 2

Cure Test of Shoulder Stiffness II

| $V_F$ (V) | Effective cure rate (%) | Skin damage rate (%) |
|---|---|---|
| 0.5 | 80 | 0 |
| 0.6 | 100 | 0 |
| 0.7 | 100 | 20 |
| 0.9 | 80 | 40 |

As seen from Table 2, the effective cure rate is very high in the $V_F$ range of 0.5 to 0.9 V, and the skin-contact type medical treatment apparatus of this embodiment is verified to be effective for physiological activation of in-vivo subcutaneous tissues. Although not shown in Table 2, the pulse frequency at each $V_F$ was in the range of 100 to 200 Hz as a mean value of five patients at the time when the apparatus was loaded. After a lapse of 24 hours, a rise of the frequency to 300 to 500 Hz was observed. This frequency rise may be ascribed to a subcutaneous impedance lowered by physiological activation of in-vivo subcutaneous tissues, the lowered impedance resulting in a short pulse period T of the equation (3).

It is to be noted that the skin damage rate rises as $V_F$ exceeds 0.6 V. This may be ascribed to a pH change of skin under the positive and negative poles to be caused by a rise of a subcutaneous current value at a high cut-off voltage, and to a biochemical tissue change by subcutaneous current stimuli.

It is preferable therefore to set $V_F$ to 0.6 V or lower if the apparatus is used for a long term. If $|V_B|\geq|V_F|$, it is preferable to set $V_B$ to 0.6 V or lower as described above.

Figure 5A:
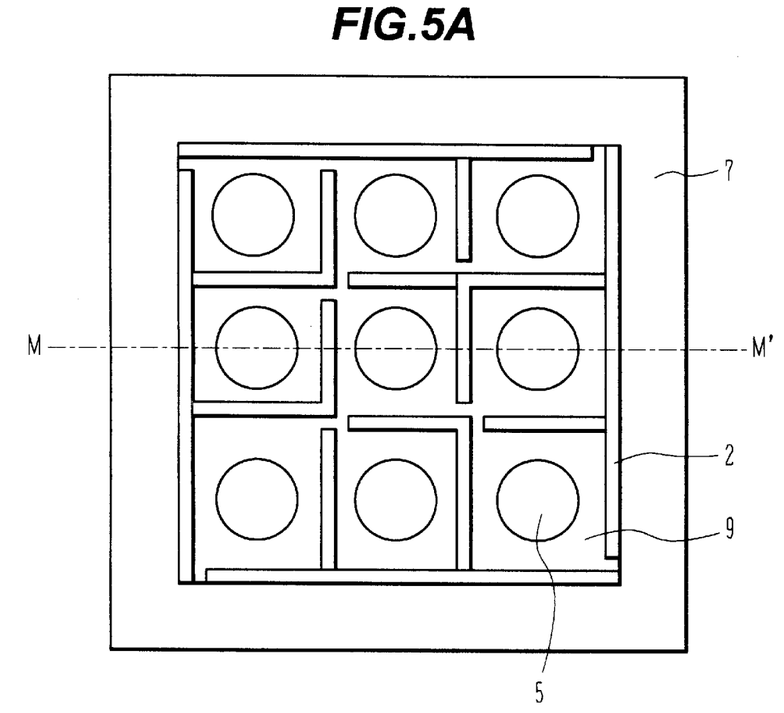
FIGS. 5A and 5B are a plan view and a cross sectional view showing the structure of a skin-contact type medical treatment apparatus according to still another embodiment of the invention.
Figure 5B:
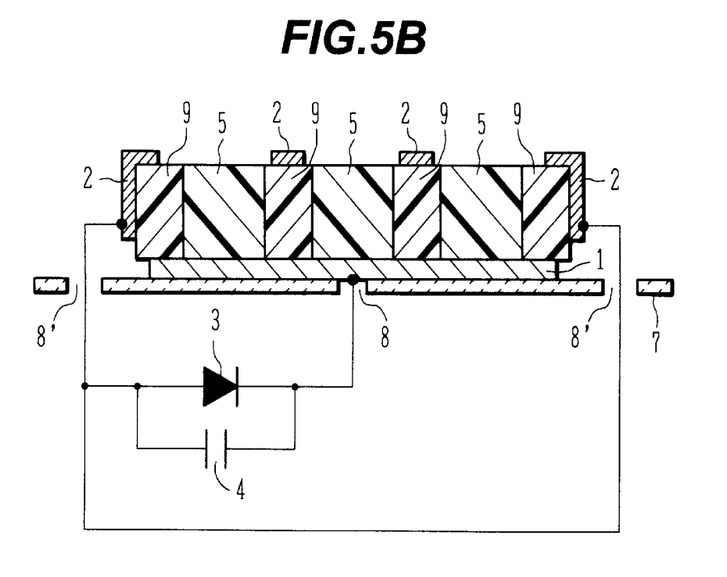

FIG. 5A is a plan view showing the structure of a device according to another embodiment, and FIG. 5B is a cross sectional view of the device taken along one-dot chain line M-M' of FIG. 5A. This device is an iontophoresis type transcutaneous dosing element having a permeating medicine layer.

A first conductive member 1 is adhered to the adhesive surface of a sticking cloth 7. In this embodiment, the first conductive member 1 is a copper thin plate. A medicine reservoir plate 9 having a plurality of cylindrical through holes is adhered to the first conductive member 1, the medicine reservoir plate being made of foaming polyethylene or the like having a thickness of 2 to 4 mm. A conductive medicine layer 5 is densely loaded in each cylindrical through hole, the conductive medicine layer 5 being made of conductive matrix dispersed with permeating medicine ions (in this embodiment, negative ions). Second conductive members 2 of a lattice shape are adhered on the medicine reservoir plate 9 at positions not in contact with the boarder of each cylindrical through hole. The second conductive member 2 is a tin film whose surface is covered with a manganese oxide film (n-type semiconductor). The second conductive member 2 is divided into a plural members each of which contacts to a skin at a different position from each other. Each member of the second conductive member is electrically isolated with each other on the surface of the medicine reservoir plate 9. The first and second conductive members 1 and 2 are electrically connected, via a parallel circuit of a diode 3 and a capacitor 4 formed on the side of the non-adhesive surface (surface not in contact with skin) of a sticking cloth 7, along interconnection holes formed in the sticking cloth 7.

The conductive matrix is water soluble cream containing sodium chloride of 1 wt %, and is dispersed with magnesium-L-ascorbyl 2-phosphate of 2 mol % as permeating medicine. $V_B$ of the constant voltage diode 3 ($|V_B|>|V_F|$) was –0.6 V, and the capacitance of the capacitor 4 was 20 pF.

This device was attached to each rat with back hairs being cut, by using the adhesive surface of the sticking cloth 7. SD male rats were used for checking a concentration change of ions permeated into blood for each group of four rats, by using a load time as a parameter. It was confirmed that both the manganese oxide film of the second conductive member and the conductive matrix become in contact with skin when the device is loaded. The pulse frequency indicating a change in the voltage across the diode 3 was 300 Hz (mean value) when measured at the time of loading.

For comparison, the parallel circuit of the diode 3 and capacitor 4 were disconnected and the first and second conductive members 1 and 2 were directly connected on the non-adhesive surface of the sticking cloth 7. The other structure, material, and size of this transcutaneous dosing element are the same as those of FIGS. 5A and 5B. This device was loaded to each SD male rat with back hairs being cut, one device for each rat.

Figure 6:
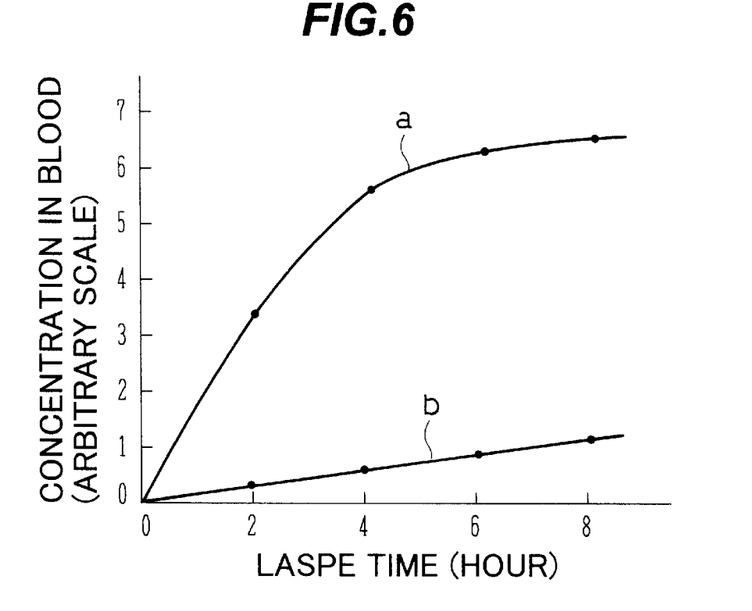
FIG. 6 is a graph showing the concentration change of ions of medicine permeated into blood through iontophoresis by using the skin-contact type medical treatment apparatus constructed as in FIGS. 5A and 5B.

The concentration change of ascorbic acid in blood was measured after 2, 4, 6,and 8 hours after the transcutaneous dosing element was loaded. Blood was collected from each rat and analyzed by gas-liquid chromatography. The results are shown in FIG. 6. The abscissa of FIG. 6 indicates a lapse time in the unit of hour, and the ordinate indicates a concentration in blood in an arbitrary scale. A curve a shows the concentration obtained by using the medical treatment apparatus shown in FIGS. 5A and 5B, and a curve b shows the concentration obtained by using the medical treatment apparatus formed for comparison.

As seen from this graph, use of the skin-contact type medical treatment apparatus of this embodiment allows a dose at a concentration 5 to 6 times as high as the comparison apparatus. With the comparison apparatus, the concentration in blood gradually increases as the time lapses, and is not stable even after a lapse of 8 hours. With the embodiment apparatus, the concentration in blood becomes generally constant after about 4 hours. Although not shown, a time required for saturation of the concentration in blood depends upon a combination of first and second conductive members. It has been found that this time becomes shorter as the combination has a larger internal electromotive force of a bio-cell.

Iontophoresis was performed for medicine having positive ions as its effective components and for neutral medicine, by using the skin-contact type medical treatment apparatuses having the same structure as that shown in FIGS. 5A and 5B and the skin-contact type medical treatment apparatuses having the same structure as the above-described comparison apparatus. In this embodiment, however, the positions of the first and second conductive members 1 and 2 shown in FIGS. 5A and 5B were exchanged. Namely, copper of the first conductive member 1 was shaped into a lattice pattern and adhered to the contact surface of the apparatus, and manganese oxide of the second conductive member 2 was shaped into a flat plate and adhered to the adhesive surface of the sticking cloth 7 to be in contact with the conductive medicine layer 5. The diode 3 used was a backward diode ($|V_F|>|V_B|$) and $V_F$ was 0.6 V. The capacitance of the capacitor 4 was 20 pF. The conductive matrix has a creamy base material containing NaCl and dispersed with carnitine hydrochloride or α-tocopherol.

Figure 7:
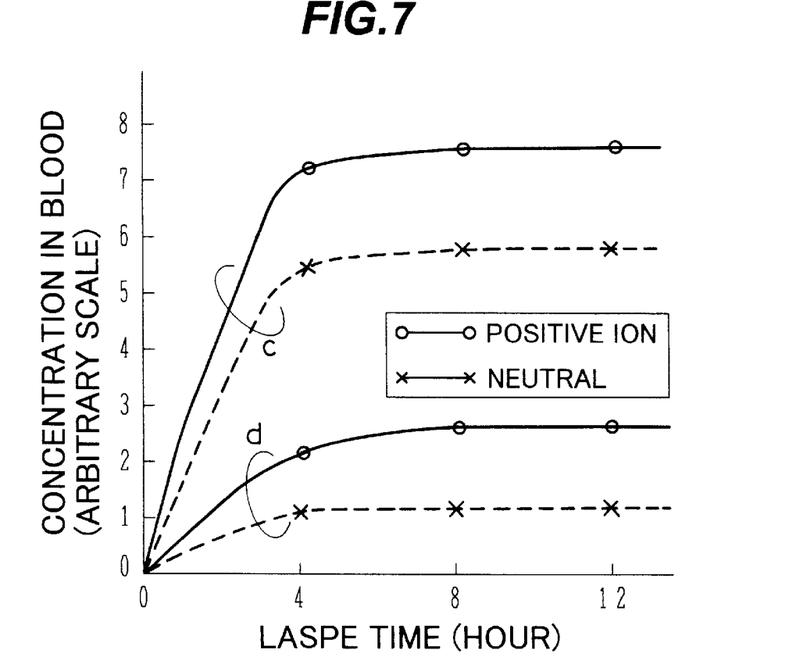
FIG. 7 is a graph showing the concentration change of ions of another medicine permeated into blood through iontophoresis by using the skin-contact type medical treatment apparatus constructed as in FIGS. 5A and 5B.

Iontophoresis was performed for each group of three SD male rats by loading the apparatus on each rat with back hairs being cut, and the concentration in blood was measured. The results are shown in FIG. 7. The abscissa indicates a lapse time in the unit of hour, and the ordinate indicates a concentration in blood in an arbitrary scale. A circle symbol is for medicine having positive ion as its effective components, and a cross symbol is for neutral medicine. A group c uses the medical treatment apparatus having the structure shown in FIGS. 5A and 5B, and a group d uses the comparison apparatus. The pulse bias method of this embodiment can realize effective permeation 3 to 5 times greater than the d.c. bias only of the bio-cell. Although not shown, it has been found that a difference of effective permeation becomes large as the molecular weight of ions becomes large. If medicine is simply coated without using iontophoresis, the concentration of ions permeated into blood lowers by about one digit as compared to the concentration shown in FIG. 7.

Magnets may be mounted on the transcutaneous dosing element shown in FIGS. 5A and 5B. The magnets have a magnetic force sufficiently large for influencing the motion of ions permeating into skin and a magnetic field having vertical components to the direction of permeation of medicine ions (generally the vertical direction to a skin surface). Under the influence of this magnetic field, medicine ions permeated into skin diffuse from permeated sites in a circular motion. It is therefore possible to lower the medicine concentration just under the skin contact portions and prevent to cause a counter electromotive force for bio-cell generation of electric power. A permanent magnet having a magnetic flux density of 1000 to 2000 gausses hardly affects the characteristics of the diode 3 and capacitor 4 so that the characteristics of a pulse waveform, frequency, peak value, and the like are not changed.

Figure 8:
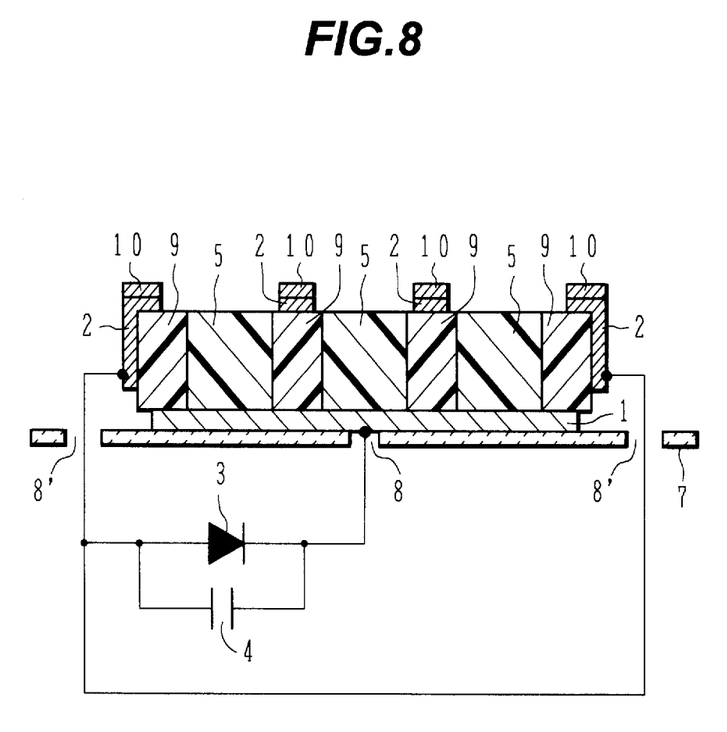
FIG. 8 is a cross sectional view of a skin-contact type medical treatment apparatus according to a modification of the embodiment shown in FIGS. 5A and 5B.

As shown in FIG. 8, in the medical treatment apparatus shown in FIGS. 5A and 5B, a thin solid electrolyte 10 may use in contact with the electrode (first or second conductive member 1 or 2) which is not in contact with the conductive medicine layer 5, to form skin contact via this solid electrolyte 10. In this case, it was confirmed by using the same kind of medicine ions that permeation of medicine ions was improved by 2 to 3 times per unit time. In the medicine permeation experiments (negative ions as effective components) shown in FIG. 6, the first conductive member 1 contacts the conductive medicine layer 5 and the second conductive member 2 contacts the solid electrolyte 10. Therefore, the conductive medicine layer 5 and solid electrolyte 10 become in contact with skin. In the medicine permeation experiments (positive ions as effective components, or neutral medicine) shown in FIG. 7, the first conductive member 1 contacts the solid electrolyte 10 and the second conductive member 2 contacts the conductive medicine layer 5.

The solid electrolyte 10 suitable for use is a material which shows a relatively high ion conductivity near at a body temperature and has less stimulus to skin. Such material may be SPE (proton conductor) of carbon fluoride, Na-$\beta$Al$_2$O$_3$ (sodium ion conductor), Li$_3$N (lithium ion conductor), and the like. A solvent type ion conductor may be used which is made of water soluble cream dispersed with biological brine.

Acceleration of the iontophoresis effects by the solid electrolyte 10 in contact with the electrode is achieved by a greatly lowered skin contact resistance value. It was confirmed that the subcutaneous current value increased by 2 to 3 times.

The invention has been described with reference to the preferred embodiments. The invention is not limited to the above embodiments only. For example, the first conductive member 1 may be noble metal or its alloy, in addition to gold and copper used in the above embodiments. The second conductive member 2 may be various kinds of oxide semiconductor having a suitable standard single-electrode potential, such as tin oxide, magnesium alloy oxide and titanium oxide, various kinds of non-oxide semiconductor, such as germanium, zinc sulfide, and indium phosphide, in addition to semiconductors (zinc oxide, manganese oxide, aluminum oxide) used in the above embodiments.

It is apparent that various modifications, improvements, combinations, and the like can be made by those skilled in the art.

I claim:

1. A skin-contact type medical treatment apparatus comprising:

a first conductive member having a contact surface made of single metal or alloy;

a second conductive member having a contact surface made of semiconductor, a standard single-electrode potential of the semiconductor constituting the contact surface of said second conductive member being lower than a standard single-electrode potential of the metal constituting the contact surface of said first conductive member; and a parallel circuit of a diode and a capacitor electrically connected to said first and second conductive members.

2. A skin-contact type medical treatment apparatus according to claim 1, wherein said diode is connected so that a direction of current flowing from said first conductive member to said second conductive member via said diode becomes a backward direction if a forward current rise voltage of said diode is lower than a backward breakdown voltage, and that a direction of current flowing from said first conductive member to said second conductive member via said diode becomes a forward direction if a forward current rise voltage of said diode is higher than a backward breakdown voltage.

3. A skin-contact type medical treatment apparatus according to claim 1, further comprising a conductive medicine layer provided in contact with the contact surface of one of said first and second conductive members, said conductive medicine layer including matrix dispersed with effective medicine components and conductive ions at least capable of permeating into skin.

4. A skin-contact type medical treatment apparatus according to claim 1, further comprising a protective resistor element inserted serially to the parallel circuit of said diode and said capacitor.

5. A skin-contact type medical treatment apparatus according to claim 4, wherein a product of capacitance of said capacitor and resistance of closed circuit being composed of said first conductive member, skin, said second conductive member, said parallel circuit, and said protective resister element is 0.002 seconds or longer and 0.1 second or shorter.

6. A skin-contact type medical treatment apparatus according to claim 1, further comprising a solid electrolyte provided in contact with the contact surface of one of said first and second conductive members not provided with said conductive medicine layer.

7. A skin-contact type medical treatment apparatus according to claim 1, wherein the forward current rise voltage of said diode is 0.6 V or lower and the backward breakdown voltage is 0.6 V or higher.

8. A skin-contact type medical treatment apparatus according to claim 1, wherein the backward breakdown voltage of said diode is 0.6 V or lower, and the forward current rise voltage is larger than the backward breakdown voltage.

9. A skin-contact type medical treatment apparatus according to claim 1, wherein said capacitor is a junction capacitor of said diode.

10. A skin-contact type medical treatment apparatus according to claim 1, wherein the metal constituting the contact surface of said first conductive member is at least one metal selected from a group consisting of gold, copper, other noble metals, and alloys of these metals.

11. A skin-contact type medical treatment apparatus according to claim 1, wherein the semiconductor constituting the contact surface of said second conductive member is made of at least one material selected from a group consisting of zinc oxide, manganese oxide, aluminum oxide, tin oxide, magnesium alloy oxide, titanium oxide, germanium, zinc sulfide, and indium phosphide.

12. A skin-contact type medical treatment apparatus according to claim 1, wherein said second conductive member is divided into a plural members each of which contacts to a skin at a different position from each other.

* * * * *